US009333109B2

(12) United States Patent
Kuromiya et al.

(10) Patent No.: US 9,333,109 B2
(45) Date of Patent: May 10, 2016

(54) MOTION ASSIST APPARATUS

(71) Applicant: HONDA MOTOR CO., LTD., Minato-ku, Tokyo (JP)

(72) Inventors: Yasuhito Kuromiya, Saitama (JP); Hiroyuki Goto, Saitama (JP); Makoto Nakatsuka, Saitama (JP); Hideo Shimizu, Saitama (JP); Tatsuya Ishikawa, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 14/717,030

(22) Filed: May 20, 2015

(65) Prior Publication Data

US 2015/0335461 A1    Nov. 26, 2015

(30) Foreign Application Priority Data

May 23, 2014    (JP) ................................. 2014-107256

(51) Int. Cl.
| | | |
|---|---|---|
| *F16M 13/00* | (2006.01) | |
| *A61F 5/02* | (2006.01) | |
| *B25J 9/00* | (2006.01) | |
| *F16M 13/04* | (2006.01) | |

(52) U.S. Cl.
CPC ................. *A61F 5/02* (2013.01); *B25J 9/0006* (2013.01); *F16M 13/04* (2013.01)

(58) Field of Classification Search
CPC .......... A61F 5/02; B25J 9/0006; F16M 13/04
See application file for complete search history.

(56) References Cited

U.S. PATENT DOCUMENTS

| 5,433,201 A | 7/1995 | Manthey | |
|---|---|---|---|
| 9,022,956 B2 * | 5/2015 | Kazerooni | ................ A61F 5/01 601/5 |
| 2011/0105966 A1 * | 5/2011 | Kazerooni | ............. A61H 3/008 601/35 |

FOREIGN PATENT DOCUMENTS

| DE | 4214523 A1 | 11/1993 |
|---|---|---|
| JP | 2736619 B2 | 4/1998 |
| WO | 2012/171000 A1 | 12/2012 |

OTHER PUBLICATIONS

Examination Report issued Oct. 15, 2015 in the corresponding DE Patent Application 10 2015 209 329.8 and the English translation thereof.
Search Report issued Oct. 15, 2015 in the corresponding DE Patent Application 10 2015 209 329.8 and the English translation thereof.

* cited by examiner

*Primary Examiner* — Amy Sterling
(74) *Attorney, Agent, or Firm* — Carrier Blackman & Associates, P.C.; William D. Blackman; Joseph P. Carrier (57) ABSTRACT

The present invention provides a motion assist apparatus capable of reducing the discomfort of a user that may be caused when a motion is assisted. A motion assist apparatus 1 has actuators 11, which apply a force for controlling the posture of the upper body of a user P through the intermediary of a second frame 14, a posture estimation sensor PS, which detects a posture angle θ of the upper body of the user P, a control unit C, which controls the actuators 11 to reduce a deviation dθ of a posture angle θ from a reference posture angle θ0, and a trigger sensor TS, which detects the occurrence of a trigger event. The control unit C sets the posture angle at the time of the occurrence of the trigger event as the reference posture angle θ0.

7 Claims, 7 Drawing Sheets

MOTION ASSIST APPARATUS

BACKGROUND OF THE INVENTION

1. Field of the Invention

The present invention relates to a motion assist apparatus adapted to assist a motion of an upper body to return to a basic posture from a tilted state and a motion of maintaining a tilted posture.

2. Description of the Related Art

There has conventionally been known a motion assist apparatus provided with thigh abutting members to be attached to the legs of a user, a chest abutting member to be attached to the upper body of the user, thigh support arms connected to the thigh abutting members, upper body support anus connected to the chest abutting member, and a waist abutting member to be attached to the waist of the user (refer to Japanese Patent No. 2736619 (hereinafter referred to as Patent Document 1)).

In the motion assist apparatus, a force from the elastic force of a coil spring used for connecting the thigh support arms and the waist abutting member and the elastic force of the upper body support arms themselves increases as the upper body relatively tilts with respect to legs, and the force acts to the user to increase the angle formed by the thigh support arms and the upper body support arms. This force is applied to a user to assist his or her motion to set the tilted upper body back to a basic posture (the posture in which the relative positions of the upper body and the legs have been set back to the positions at which the user is in a normal upright state).

Further, in the motion assist apparatus, the upper body support arms are vertically slidably installed with respect to the waist abutting member, and the position at which a chest abutting member connected to the upper body support arms is abutted against the user is adjustable in a vertical direction within a predetermined range.

According to the motion assist apparatus described in Patent Document 1, the force for restraining, the tilt of the upper body relative to the legs is applied to the user by the predesigned elastic forces of the constituent members. Hence, there has been a possibility that the motion assist apparatus could cause a user to feel uncomfortable when the force for assisting his or her motion is applied to the user, depending on the body shape of the user.

SUMMARY OF THE INVENTION

The present invention has been made with a view toward solving the problem described above, and an object of the invention is to provide a motion assist apparatus capable of reducing the discomfort of a user that may arise at the time of assisting his or her motion and also capable of applying an appropriate force at an appropriate posture.

A motion assist apparatus in accordance with the present invention includes: a first orthosis adapted to be attached to a leg of a user; a second orthosis adapted to be attached to an upper body of the user; a first frame connected to the first orthosis; second frame connected to the second orthosis; an actuator that applies a force to the user through the intermediary of the first orthosis and the second orthosis by transmitting a driving force to the first frame or the second frame; a posture estimation sensor that detects a posture angle of the upper body relative to a vertical plane having a longitudinal direction of the user defined as a perpendicular direction thereof; a control unit that controls the drive of the actuator such that a force for reducing a deviation of the posture angle from a reference posture angle is applied to the user; and a trigger sensor that detects an occurrence of a trigger event, wherein the control unit sets, as the reference posture angle, a posture angle detected by the posture estimation sensor in a case where the trigger sensor detects the occurrence of the trigger event.

Thus, in the motion assist apparatus in accordance with the present invention, the control unit sets, as the reference posture angle, the posture angle detected by the posture estimation sensor when the occurrence of the trigger event is detected. This arrangement makes it possible to adjust the magnitude of a force acting on the user or the position at which the force is applied according to the basic posture (the posture in which the relative position between the upper body and the legs is the position when the user is in a normal upright state), which differs from one user to another.

Further, the control unit of the motion assist apparatus in accordance with the present invention controls the actuator according to the set reference posture angle such that the force to be applied, to the user reduces the deviation of the posture angle detected by the posture estimation sensor from the reference posture angle.

Hence, the motion assist apparatus in accordance with the present invention allows an appropriate force to be applied to a user on the basis of the tilt of the upper body of the user according to the basic posture, which differs from one user to another. Therefore, the motion assist apparatus in accordance with the present invention makes it possible to reduce the discomfort to the user, which may be caused when assisting his or her motion.

In the motion assist apparatus in accordance with the present invention, preferably, the trigger sensor is a force sensor that detects a magnitude of the force to be applied by the actuator in order to control a tilt of the upper body relative to the vertical plane, which has the longitudinal direction of the user defined as the perpendicular direction thereof, and the control unit drives the actuator such that a gap between the second orthosis and the user in a basic posture is reduced and sets as a reference posture angle, the posture angle detected by the posture estimation sensor in a case where the force detected by the force sensor reaches a predetermined value or as value in as predetermined range.

The foregoing configuration that uses the force sensor as the trigger sensor allows the reference posture angle to be automatically set, thus making it easier to reduce the discomfort to the user.

Further, in the motion assist apparatus in accordance with the present invention, preferably, the trigger sensor is a setting switch through which the user inputs a signal at an arbitrary timing, and the control unit sets, as the reference posture angle, a posture angle detected by the posture estimation sensor when a signal from the setting switch is detected.

The configuration that enables the user to set an arbitrary angle as the reference posture angle allows an appropriate reference posture angle to be easily set, thus making it possible to more easily reduce the discomfort to the user.

Further, in the motion assist apparatus in accordance with the present invention, preferably, the second orthosis has an abutting member, which is on a user side and which abuts against the user, and a fixing position of the abutting member can be changed in a vertical direction with respect to the second frame.

The abutting position that allows the force for controlling the posture to be applied without causing discomfort to the user differs according to the body shape of the user. Therefore, the configuration that makes it possible to change the fixing position of the abutting member, which directly applies the force to the user, relative to the second orthosis allows the position, at which the force is applied, to be changed according to the body shape of the user. This permits further easier reduction in the discomfort to the user.

Further, in the motion assist apparatus in accordance with the present invention, preferably, the second orthosis has, on the user side, an abutting member that comes in contact with the user, and the abutting member has a round shape when the user is observed from the side.

This arrangement allows the abutting member to be easily abutted at a proper angle regardless of the difference in body shape of the user.

Further, in the motion assist apparatus in accordance with the present invention, preferably, an abutting member is installed at a portion of the second orthosis that comes in contact with the user, and the abutting member is rotatable about an axis line parallel to a lateral direction of the user with respect to the second orthosis.

With this arrangement, the abutting member is more easily abutted at a proper angle regardless of the difference in body shape of the user than the case of a configuration in which the abutting member of the second orthosis connected to the second frame is fixed with respect to the second orthosis.

Further, in the motion assist apparatus in accordance with the present invention, preferably, the second orthosis has an abutting member, which comes in contact with the user, on a front side of the user, and the abutting member has a size in a lateral direction which covers an area from a joint part of a sixth rib and a sixth costal cartilage on a right side of the user to a joint part of a sixth rib and a sixth costal cartilage on a left side and an area from a joint part of a seventh rib and a seventh costal cartilage on the right side of the user to a joint part of a seventh rib and a seventh costal cartilage on the left side, and the abutting member has a size in a vertical direction which covers an area from the joint part of the sixth rib and the sixth costal cartilage on the right side of the user to a joint part of the seventh rib and the seventh costal cartilage on the right side, and an area from the joint part of the sixth rib and the sixth costal cartilage on the left side of the user to the joint part of the seventh rib and the seventh costal cartilage on the left side.

If the abutting position of the abutting member is set above the sixth rib, then the abutting member will come in contact with the chest. On the other hand, if the abutting position of the abutting member is set below the seventh rib, then the abutting member will come in contact with a body surface area where an ensiform cartilage (breastbone) or the like is located. For these reasons, the position of the abutting member is frequently adjusted such that the force for assisting a motion is applied to the sixth rib and the seventh rib.

Therefore, adjusting the size of the abutting member such that the abutting member covers the joint part of the sixth costal cartilage and the sixth rib and the joint part of the seventh costal cartilage and the seventh rib makes it even easier to reduce the discomfort to the user. Further, the abutting member adjusted to the foregoing size will not interfere with the motions of the arms of the user.

BRIEF DESCRIPTION OF THE DRAWINGS

FIGS. 3A to 3C present diagrams illustrating the schematic configurations of a second frame and a second orthosis of the motion assist apparatus illustrated in FIG. 1, wherein

FIGS. 5A to 5D present graphs illustrating the force applied to a user on the basis of the difference between a reference posture angle of the motion assist apparatus illustrated in FIG. 1 and a posture angle, wherein

DESCRIPTION OF THE PREFERRED EMBODIMENTS

First, the configuration of a motion assist apparatus according to the present embodiment will be described with reference to FIG. 1, FIG. 2, and FIGS. 3A to 3C.

Figure 1:
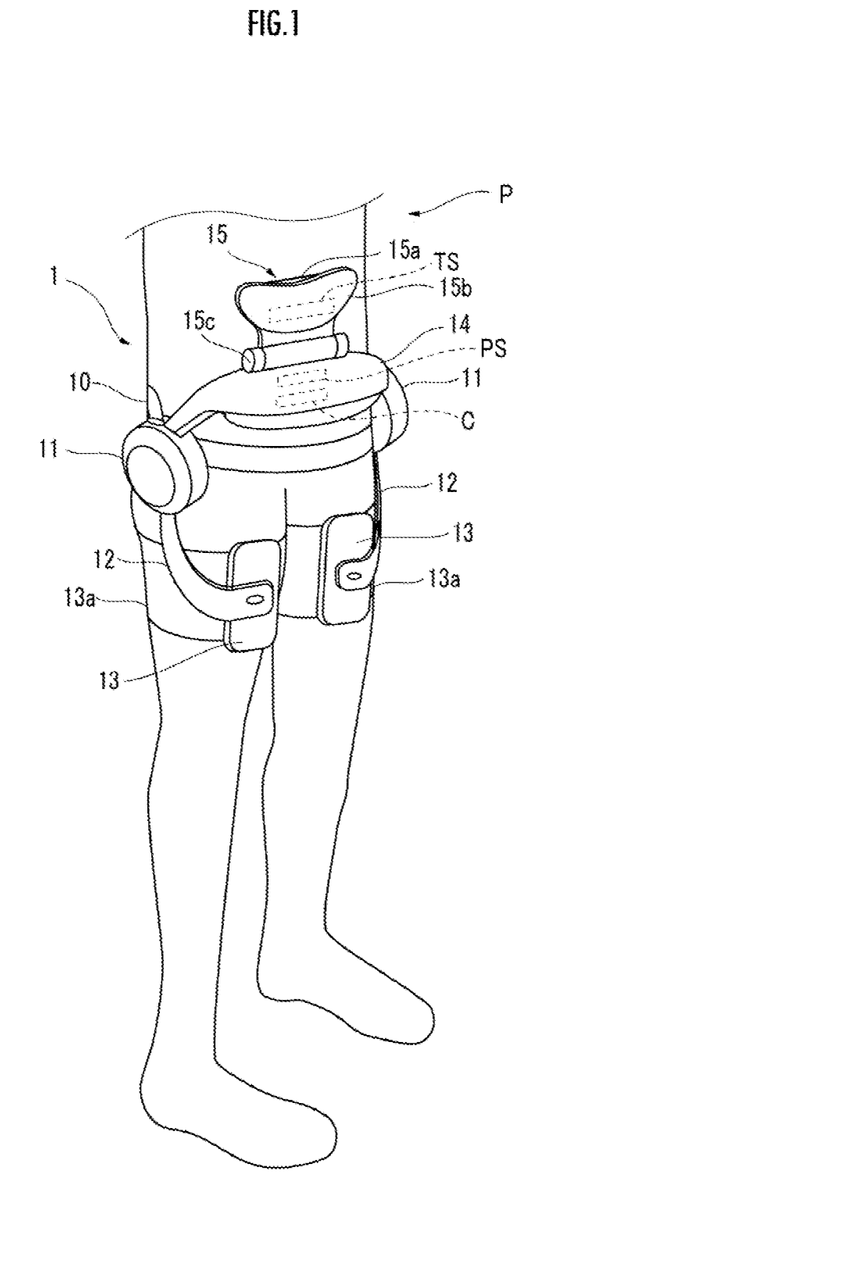
FIG. 1 is a perspective view illustrating the schematic configuration of a motion assist apparatus according to an embodiment of the present invention.

As illustrated in FIG. 1, a motion assist apparatus 1 is provided with a waist belt 10 to be attached to the waist of a user P, and a pair of left and right actuators 11 to be attached to the vicinity of the waist of the user P by the waist belt 10 when the user P puts on the motion assist apparatus 1.

The motion assist apparatus 1 is further provided with a pair of left and right first frames 12, which extend from the bottoms of each of the actuators 11 to the fronts of the thighs of the user P, and first orthoses 13, which are connected to the bottom ends of each of the first frames 12 and which are to be attached to the left and the right legs of the user P.

The motion assist apparatus 1 is further provided with a second frame 14, which extends from the tops of the actuators 11 to the front of the upper body (a portion above the rotational axis of a hip joint) of the user P, and a second orthosis 15, which is connected to the top edge of the second frame 14 and which is to be attached to the upper body of the user P. The actuators 11 do not have to be necessarily attached to the vicinity of the waist and may be disposed at other places. Further, the first frames 12 and the second frame 14 are rotatably connected through the intermediary of the actuators 11; alternatively, however, the first frames 12 and the second frame 14 may be directly and rotatably connected.

The second frame 14 includes a posture estimation sensor PS and a control unit C, which controls the drive of the actuators 11. The posture estimation sensor PS detects the angle formed by a vertical plane, which has a longitudinal direction of the user P defined as a perpendicular direction thereof, and the second frame 14 (hereinafter referred to as "the posture angle θ"; refer to FIG. 2).

The posture angle θ in the present embodiment is an angle that decreases as the posture angle of the upper body of the user P with respect to the vertical plane, which has the longitudinal direction of the user P defined as the perpendicular direction thereof (the angle formed by the centerline of the upper body (the abdomen and the chest) and the vertical plane when the user P is observed from the side), decreases.

Each of the actuators 11 includes an angle sensor (not illustrated). The angle sensor detects the angle formed by the first frames 12 and the second frame 14 (hereinafter referred to as "the tilt angle φ"; refer to FIG. 2).

The tilt angle φ in the present embodiment is an angle that increases as the relative tilt angle of the upper body with respect to the legs of the user P (the angle formed by the centerline of the upper body (the abdomen and the chest) and the centerlines of the legs (the thighs) when the user P is observed from the side) increases. Hence, if the tilt angle φ is smaller than the tilt angle in a basic posture (a basic tilt angle φ0), then it can be determined that the user P is leaning forward (bending forward).

The pair of the left and right first frames 12 is configured to be independently swingable in the longitudinal direction of the user P with respect to the second frame 14 through the intermediary of the actuators 11. The first frames 12 are swung by a driving force transmitted from the actuators 11.

The first orthoses 13 have leg belts 13a. The first frames 12 and the first orthoses 13 are fixed by attaching the leg belts 13a to the thighs of the user P such that the first frames 12 and the first orthoses 13 move integrally with the legs of the user P.

The lengths of the first frames 12, the fixing positions of the first orthoses 13, and the method for fixing the first orthoses 13 to the legs of the user P are not limited to those described above insofar as the first frames 12 are configured to be swingable integrally with the legs of the user P. For example, the leg belts 13a may be omitted, and the first orthoses 13 may be slightly pressed against the legs of the user P at all times by using elastic members or the like. Further, the first orthoses 13 may be fixed to the crura rather than the thighs of the user P.

The second frame 14 is rotatably connected to the first frames 12 through the intermediary of the actuators 11. Hence, when a force is applied to the user P by the first frames 12, the second frame 14 swings in the longitudinal direction of the user P about the position, at which the second frame 14 is connected to the first frames 12, due to the reaction of the force.

The second orthosis 15 has a pad 15a, which is an abutting member, on the user P side. Further, the second orthosis 15 has a force sensor (not illustrated), which detects a force applied to the upper body of the user P from the second orthosis 15.

The pad 15a of the second orthosis 15 is formed in a semicircle, the sectional shape of which in the vertical direction has a convex surface facing the user P. In other words, the pad 15a has a round shape when the user P is observed from the side. This enables the pad 15a to be abutted against the user P at a proper angle independently of the body shape of the user P. The round shape of the pad 15a when the user P is observed from the side may be, for example, a semispherical shape or a semielliptical shape or the like.

Figure 3A:
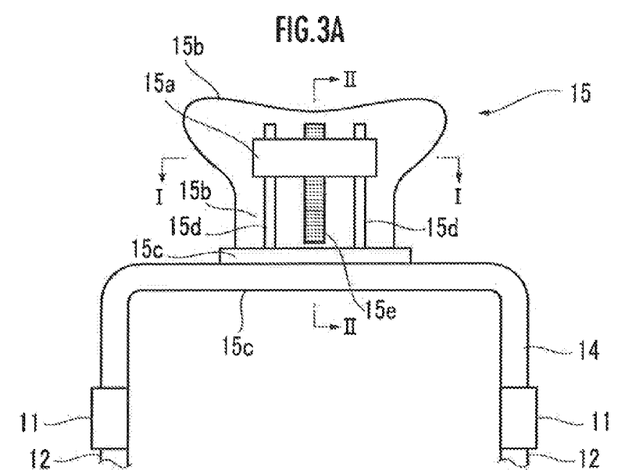
FIG. 3A is a back view.
Figure 3B:
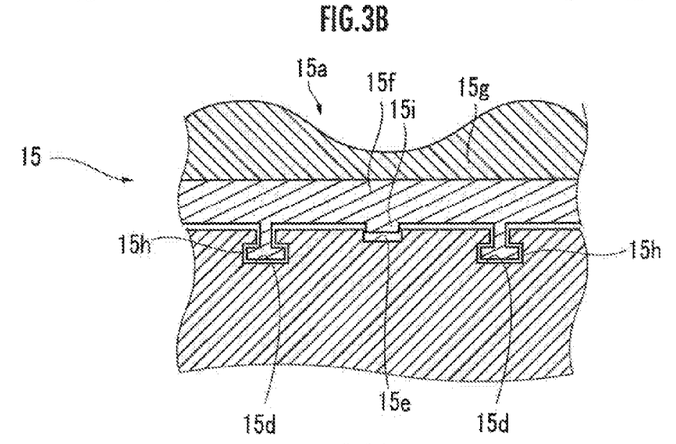
FIG. 3B is a sectional view taken along line I-I of FIG. 3A.
Figure 3C:
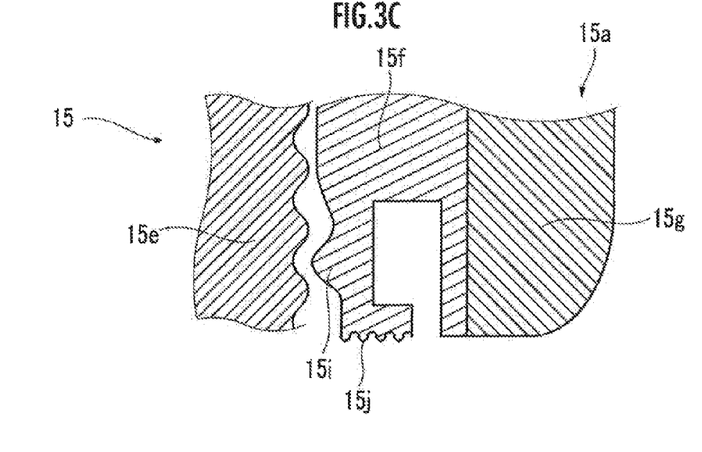
FIG. 3C is a sectional view taken along line II-II of FIG. 3A.

The pad 15a may be configured to be rotatable within a predetermined range about an axis line, which is parallel to the lateral direction of the user P, with respect to a main body 15b of the second orthosis 15 (refer to FIGS. 3A to 3C). Alternatively, the pad 15a may be formed to have a round shape and configured to be rotatable.

As illustrated in FIG. 3A, the second orthosis 15 has the main body 15b and a hinge section 15c, which connects the main body 15b to the second frame 14. The hinge section 15c makes it possible to change the angle, at which the main body 15b is fixed to the second frame 14, in the longitudinal direction of the user P.

Further, the back side (on the user P side) of the main body 15b is provided with a pair of guiderail grooves 15d, which are formed in the vertical direction to fix the pad 15a, and a latch section 15e, which is adjacent to the main body and which is formed in the vertical direction between the pair of the guiderail grooves 15d.

As illustrated in FIG. 3B, the pad 15a of the second orthosis 15 is constituted of a pad base 15f, which is movably connected to the main body 15b, and a pad section 15g, which is installed on the surface of the pad base 15f on the user P side and which is formed of an elastic member, such as a rubber member.

Further, in the pad 15a, a force sensor (not illustrated) is installed, between the pad base 15f and the pad section 15g. The force sensor may use, for example, a surface pressure sensor, a pressure sensor or a multi-axis force sensor.

The pad base 15f has projections 15b formed adjacently to the main body 15b. The projections 15h are in meshing engagement with the guiderail grooves 15d formed in the main body 15b to fix the pad 15a such that the pad 15a is slidable in the vertical direction with respect to the main body 15b.

As illustrated in FIG. 3C, below the pad base 15f, there is a latch section 15i adjacent to the pad base, and there is also a pressing section 15j provided on the bottom end of the latch section 15i adjacent to the pad base.

The latch section 15i adjacent to the pad base is formed as a plate-like member with a projecting portion matching the concave-convex surface of the latch section 15e adjacent to the main body. Further, the latch section 15i adjacent to the pad base is formed of an elastic material, and bends when the pressing section 15j is depressed by a finger, thus clearing the engagement thereof from the latch section 15e adjacent to the main body.

In the second orthosis 15 configured as described above, the fixing position of the pad 15a is vertically changeable with respect to the main body 15b (i.e. with respect to the second frame 14). Hence, the position at which a force is applied can be easily adjusted according to the body shape of the user P.

If the position at which the pad 15a is abutted is above the sixth rib of the user P, then the pad 15a will be abutted against the chest, and if the position at which the pad 15a is abutted is below the seventh rib of the user P, then the pad 15a will be abutted against the ensiform cartilage. (breastbone) or the viscera. Accordingly, the position at which the pad 15a is abutted against is frequently adjusted to the position where the sixth rib and the seventh rib of the user P are located.

Figure 4:
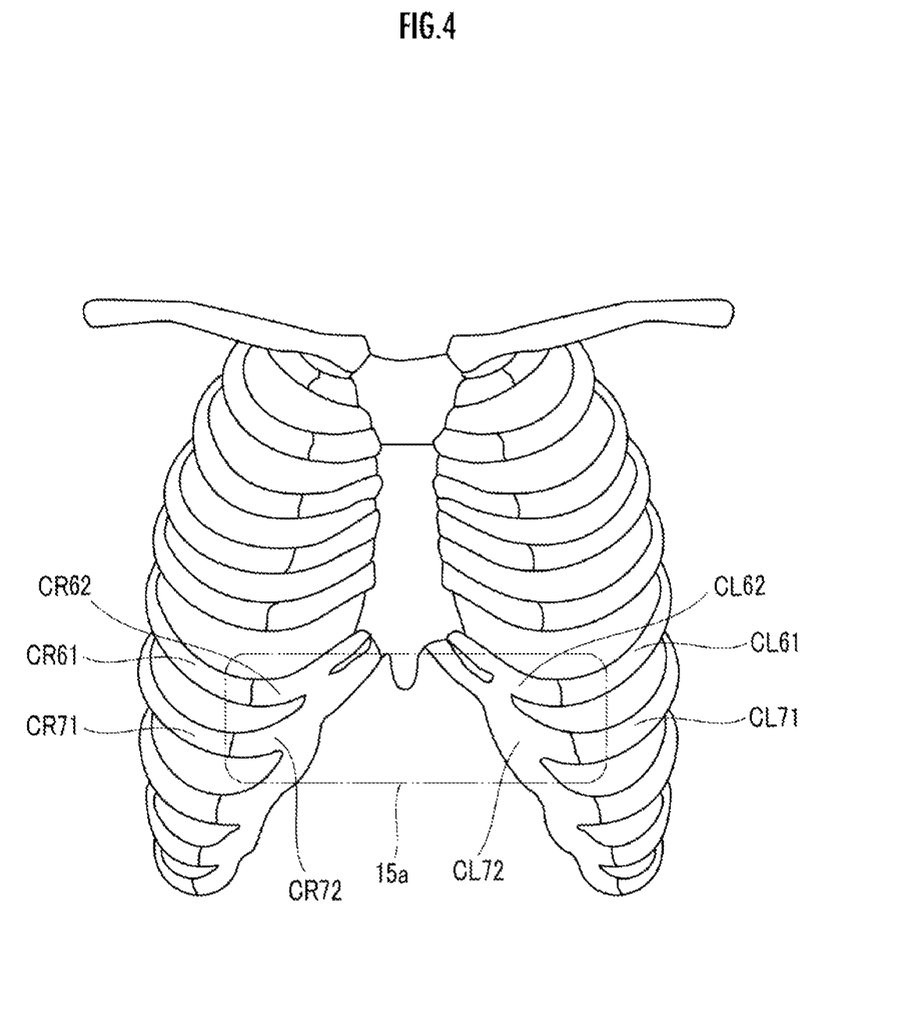
FIG. 4 is a diagram illustrating the size of a pad of the motion assist apparatus illustrated in FIG. 1.

As illustrated in FIG. 4, therefore, the pad 15a of the motion assist apparatus 1 according to the present embodiment has a size in the lateral direction that covers the area from a joint part of a sixth rib CR61 and a sixth costal cartilage CR62 on the right side of the user P having a standard body shape to a joint part eta sixth rib CL61 and a sixth costal cartilage CL62 on the left side and the area from a joint part of a seventh rib CR71 and a seventh costal cartilage CR72 on the right side of the user P to a joint, part of a seventh rib CL71 and a seventh costal cartilage CL72 on the left side.

Further, the pad 15a has a size in the vertical direction that covers the area from the joint part of the sixth rib CR61 and the sixth costal cartilage CR62 on the right side of the user P to the joint part of the seventh rib CR71 and the seventh costal cartilage CR72 on the right side, and the area from the joint part of the sixth rib CL61 and the sixth costal cartilage CL62 on the left side of the user P to the joint part of the seventh rib CL71 and the seventh costal cartilage CL72 on the left side.

The pad 15a of this size is not excessively larger than the width of the upper body of the user P, so that the pad 15a will not interfere with the motions of the arms of the user P.

Further, the pad 15a observed from above (refer to FIG. 3B) has two convex portions. The convex portions will be positioned to come M contact with the joint part of the sixth rib CR61 and the sixth costal cartilage CR62 and the joint part of the seventh rib CR71 and the seventh costal cartilage CR72.

Referring now to FIGS. 5A to 5D, a description will be given of the force applied to the user P by the motion assist apparatus 1 to control the leaning forward posture of the upper body with respect to the legs or to maintain a posture.

In the motion assist apparatus 1 configured as described above, the control unit C incorporated in the second frame 14 drives the actuators 11 to transmit a driving force to the first frames 12, thereby applying to the user P the force for controlling the posture of the upper body with respect to the legs through the intermediary of the first orthoses 13 and the second orthosis 15.

The force is controlled to more firmly suppress the tilt of the upper body with respect to the legs as a deviation dθ of a posture angle θ from a reference posture angle θ0 (i.e. dθ=θ0−θ) increases.

Figure 5A:
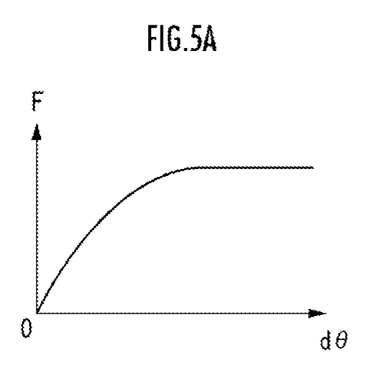
FIG. 5A is a graph illustrating a configuration in which the force increases in a curve until the difference reaches a predetermined value and the three remains constant after the difference exceeds the predetermined value

To be specific, in the motion assist apparatus 1 of the present embodiment, the control unit C controls the actuators 11 such that a force F under control increases in a curve as the deviation dθ increases in the case where the value of the deviation dθ is a predetermined value or less, and that the force F remains constant in the case where the value of the deviation dθ exceeds the predetermined value, as illustrated in FIG. 5A. The magnitude of the force F is determined on the basis of the load applied to the waist when the user P takes the leaning forward posture.

Figure 5B:
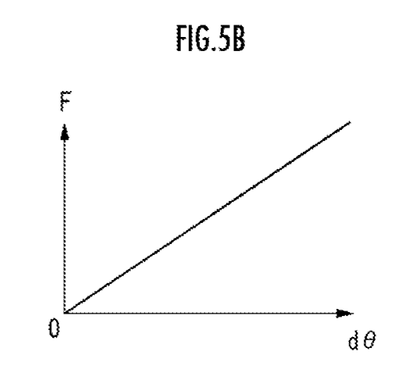
FIG. 5B is a graph illustrating a configuration in which the force linearly increases.
Figure 5C:
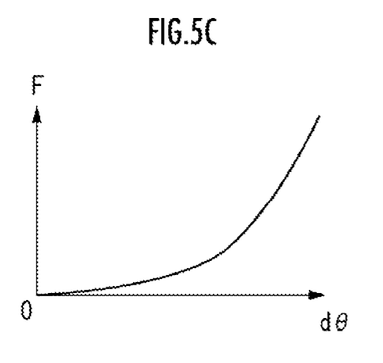
FIG. 5C is a graph illustrating a configuration in which the force increases in a curve.
Figure 5D:
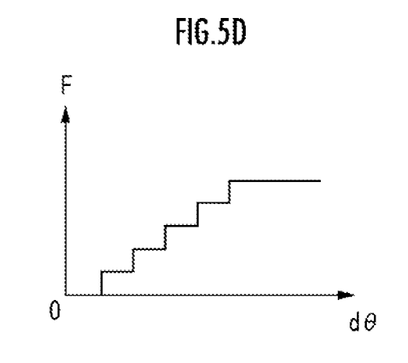
FIG. 5D is a graph illustrating a configuration in which the force increases in steps.

The force F under control for the deviation dθ does not necessarily have to be designed to change as described above. For example, the force F may be designed to linearly increase as illustrated in FIG. 5B, or to increase in a curve as illustrated in FIG. 5C, or to increase in steps as illustrated in FIG. 5D.

Figure 2:
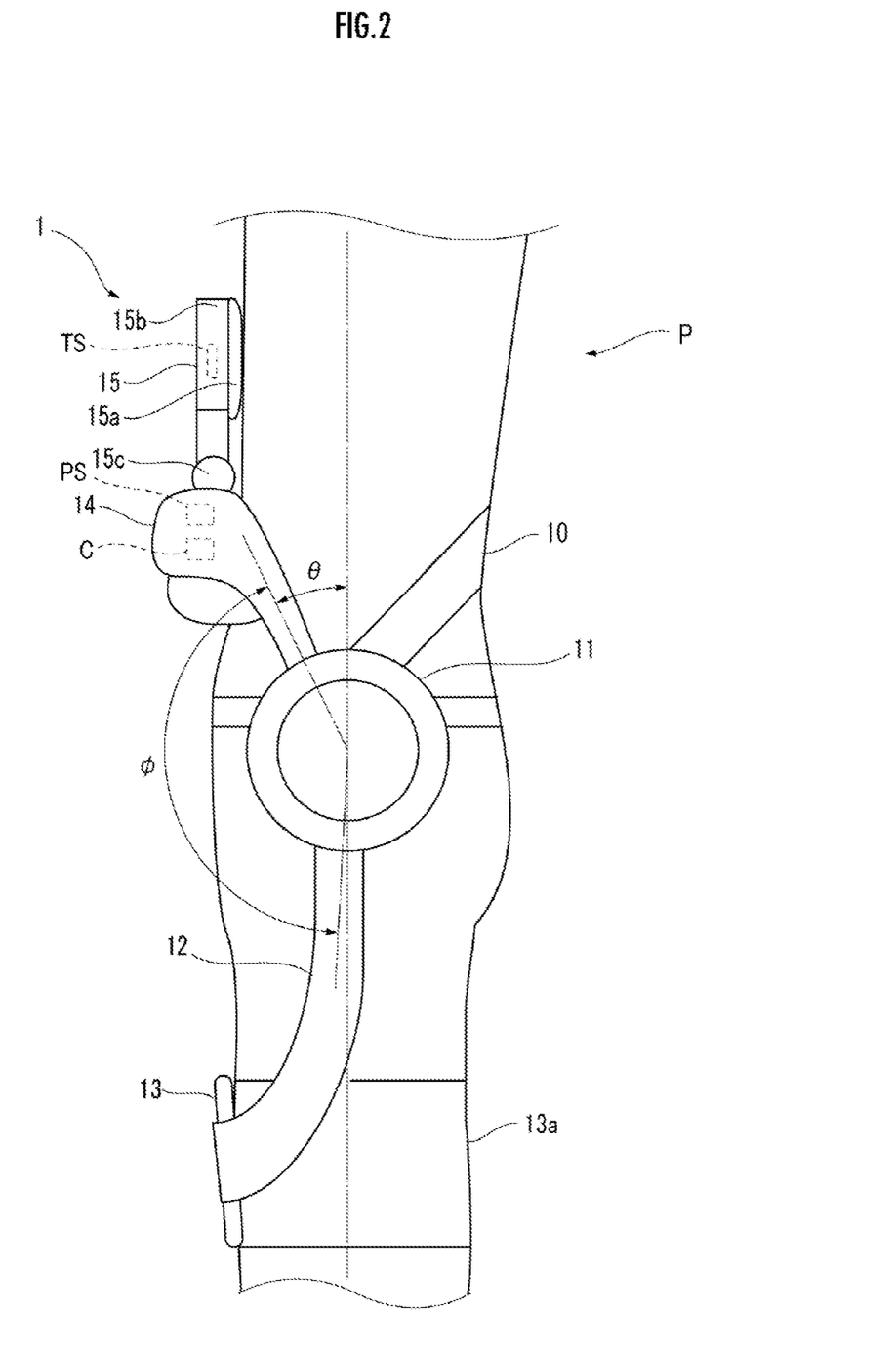
FIG. 2 is a side view illustrating the schematic configuration of the motion assist apparatus illustrated in FIG. 1.
Figure 6:
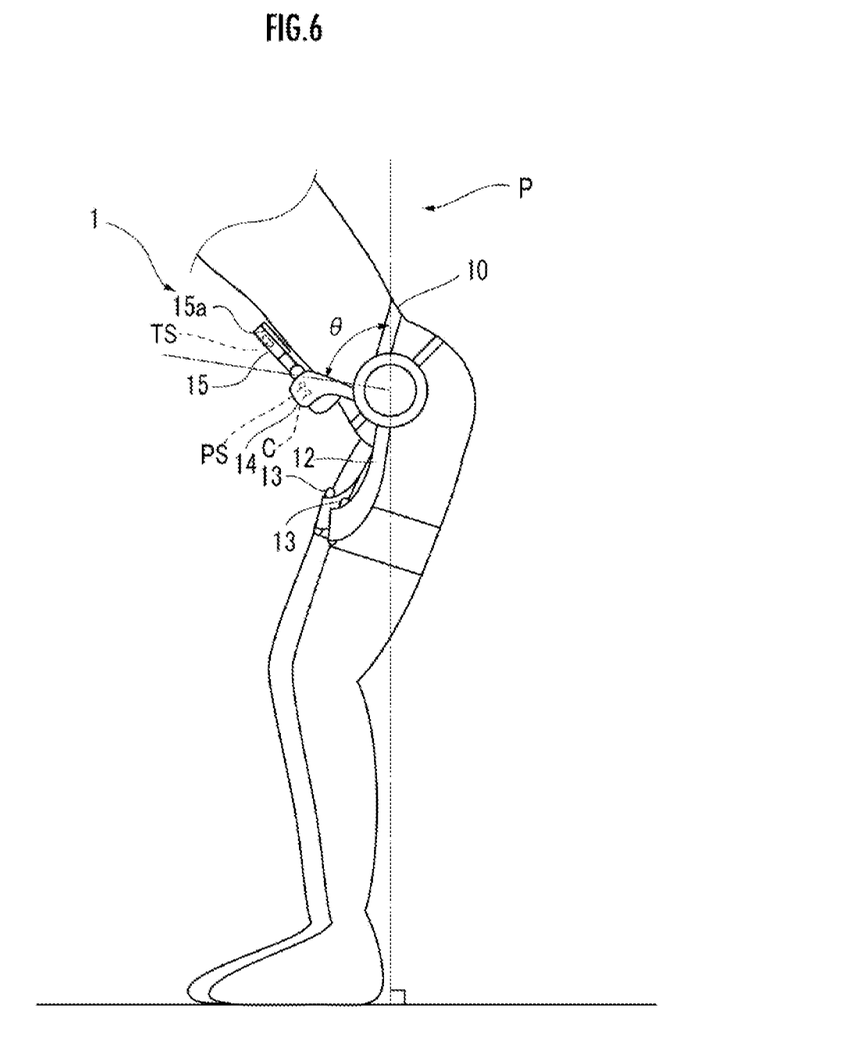
FIG. 6 is a side view illustrating a user, who is wearing the motion assist apparatus illustrated in FIG. 1 and who is leaning forward.
Figure 7:
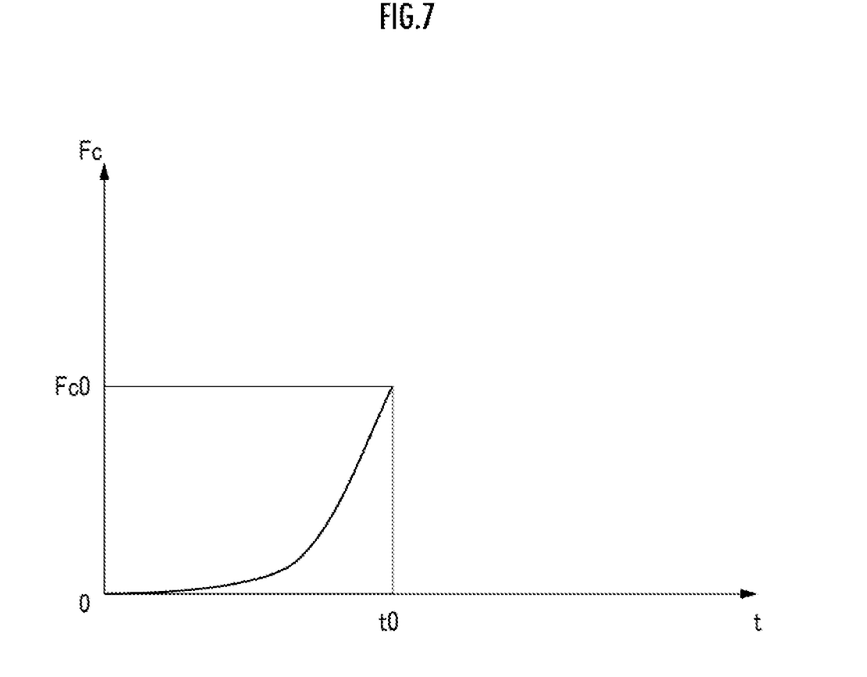
FIG. 7 is a graph illustrating the force applied to the user as time elapses at the time of the calibration of the motion assist apparatus illustrated in FIG. 1.

Referring now to FIG. 2, FIG. 6 and FIG. 7, a description will be given of how the user P uses the motion assist apparatus 1 to control the posture of his or her upper body leaning forward with respect to his or her legs.

To operate the motion assist apparatus 1 to assist the motion for changing the tilted-forward posture, in which the upper body is tilted forward with respect to the legs (the posture illustrated in FIG. 6), to the basic posture (the posture illustrated in FIG. 2 (the posture in which the relative positions of the upper body and the legs are set back to the positions at which the user is in the normal upright state)), or to assist maintaining the tilted-forward posture, the user P first puts on the motion assist apparatus 1 and then carries out calibration on the position at which the force is to be applied to the user P in order to control the posture.

To be specific, the user P first puts on the motion assist apparatus 1, and then adjusts the position of the pad 15a such that the pad section 15g is abutted against the position where the ribs of the user P are located before pressing a calibration switch (not illustrated).

At this time, when the user P takes the basic posture, the pad section 15g is stabilized at a position apart from the user P by the weight of a structure, such as the second frame 14, connected thereto. In this state, the user P presses the calibration switch (not illustrated) provided on the second frame 14 or the like.

Upon receipt of a signal from the calibration switch, the control unit C incorporated in the second frame 14 transmits the driving force to the first frames 12 from the actuators 11 and starts to apply the force to the legs of the user P through the intermediary of the first orthoses 13 connected to the first frames 12 such that the applied force gradually increases. The reaction force of the applied force causes the second orthosis 15, which is connected to the second frame 14 integrally formed with the actuators 11, to gradually approach and come in contact with the upper body of the user P. After coming in contact with the upper body, the force begins to be applied to the upper body of the user P such that the applied force gradually increases.

At this time, as time t elapses, a force Fc applied to the user P increases in a curve from the point of time at which the second frame 14 comes in contact with the user P (the point of time t=0), as illustrated in FIG. 7.

Subsequently, the control unit C stores the posture angle θ at the point of time t0 (the point of time when a trigger event takes place) when the force sensor as the trigger sensor TS incorporated in the second orthosis 15 detects a predetermined value Fc0 (e.g. a value that allows the tilt of the upper body to be controlled without causing the user P to feel uncomfortable), and sets the angle θ as the reference posture angle θ0. This completes the calibration.

The predetermined value Fc0 at this time is determined on the basis of a map stored in the control unit C. The map is established beforehand on the basis of the body shape of the user P, such as the height and the weight of the user P.

The reference angle θ0 set in the calibration does not necessarily have to be the angle obtained, when the force detected by the force sensor reaches the predetermined value Fc0, and may be an angle obtained at the point of time when the detected force takes a value within a predetermined range centering around the predetermined value Fc0.

Further, the method of calibration is not limited to the method described, above. For example, as an alternative method, a calibration switch (setting switch) may be used as a trigger sensor, and the pressing of the calibration switch by the user P may be defined as the trigger event, and the posture angle θ when the switch is pressed may be set as the reference posture angle θ0. This configuration enables the user to set any posture angle θ as the reference posture angle θ0.

By carrying out the foregoing calibration, the reference posture angle θ0 is changed from the reference posture angle tentatively set as an initial state to the reference posture angle suited to the body shape of the user P, who actually use the apparatus (i.e. the reference posture angle that matches the basic posture of the user P).

If the tilt angle φ detected by the angle sensor is smaller than the tilt angle φ0 of the basic posture after completion of the calibration, then the control unit C determines that the upper body of the user P is leaning forward with respect to the legs (i.e. bending forward (e.g. sitting on a chair or the like after a standing posture)), and the motion assist apparatus 1 applies the force for controlling the posture of the upper body tilting forward with respect to the legs to the user P.

To be specific, when the user P leans his or her upper body forward with respect to the legs as illustrated in FIG. 6, if the tilt angle φ detected by the angle sensor becomes smaller than the tilt angle φ0 of the basic posture and the posture angle θ detected by the posture estimation sensor PS becomes larger than the reference posture angle θ0, then the control unit C drives the actuators to transmit the driving force to the first frames 12 and the second frame 14.

Then, a force for the rotation toward the front of the user P (a counterclockwise force in FIG. 6) is applied to the legs of the user P from the first orthoses 13 connected to the first frames 12. As the reaction to the counterclockwise force, a force for the rotation toward the rear of the user P (a clockwise force in FIG. 6) is applied to the upper body of the user P from the second orthosis 15 connected to the second frame 14.

At this time, the control unit C controls the drive of the actuators 11 such that the force F for suppressing the tilt of the upper body with respect to the legs increases as the deviation dθ of the angle θ detected by the angle sensor from the reference angle θ0 increases (refer to FIGS. 5A to 5D).

As described above, in the motion assist apparatus 1 according to the present embodiment, the control unit C sets, as the reference posture angle θ0, the posture angle θ detected by the posture estimation sensor PS when a predetermined value (e.g. the value that allows the tilt of the upper body to be controlled without causing the user P to feel uncomfortable) is detected by the force sensor as the trigger sensor TS incorporated in the second orthosis 15 (when the occurrence of the trigger event is detected). This arrangement makes it possible to adjust the magnitude of the force to be applied to the user P and the position at which the force is to be applied according to the basic posture, which differs from one user to another.

Further, the control unit C of the motion assist apparatus 1 according to the present embodiment controls the actuators 11 according to the reference posture angle θ0 that has been set such that the force to be applied to the user P becomes the force for reducing the deviation dθ of the posture angle θ detected by the posture estimation sensor PS from the reference posture angle θ0.

Further, the control unit C of the motion assist apparatus 1 according to the present embodiment determines whether or not the user is bending forward on the basis of the relative tilt angle φ of the upper body with respect to the legs of the user P detected by the angle sensor, and controls the actuators 11 only if the user is bending forward.

Thus, the motion assist apparatus 1 according to the present embodiment makes it possible to apply an appropriate force to a user according to the tilt of the upper body of the user P on the basis of the basic posture, which is different for each user P.

Therefore, the motion assist apparatus 1 according to the present embodiment is capable of reducing the discomfort of a user that may be caused when assisting a motion. Also for seating, the three applied with respect to the tilting motion of the upper body can be properly adjusted.

Further, the motion assist apparatus in accordance with the present invention is capable of detecting the backward bending of a user from his or her basic posture by using an angle sensor that detects a relative tilt angle of the upper body with respect to the legs and capable of stopping the output of the actuators 11. This makes it possible to prevent a force from being applied in the direction of the backward bending of the user in case of a failure of the posture estimation sensor PS.

Although the description has been given of the illustrated embodiments, the present invention is not limited to the modes described above.

For example, in the foregoing embodiments, the second orthosis 15 is configured to apply the force for controlling the posture to the user P from the front. However, the motion assist apparatus in accordance with the present invention is not limited to such a configuration. For example, the second orthosis may be configured to apply a force for controlling the posture to a user from the front and the back, so that the force can be applied, also in the forward tilt direction when the upper body of the user leans backward with respect to the legs (e.g. when the user lifts an object to the height of his or her lace), thus permitting the assistance to the motion so as to reduce the load to the user caused by excessive stretching of his or her waist.

DESCRIPTION OF REFERENCE NUMERALS

1 . . . Motion assist apparatus; 10 . . . Waist belt; 11 . . . Actuators; 12 . . . First frame; 13 . . . First orthosis; 13a . . . Lev. belt; 14 . . . Second frame; 15 . . . Second orthosis; 15a . . . Pad (Abutting member); 15b . . . Main body; 15c . . . Hinge section; 15d . . . Guiderail groove; 15e . . . Latch section adjacent to the main body; 15f . . . Pad base; 15g . . . Pad section; 15h . . . Projection; 15i . . . Latch section adjacent to the pad base; 15j . . . Pressing section; C . . . Control unit; P . . . User; PS . . . Posture estimation sensor; and TS . . . Trigger sensor

What is claimed is:

1. A motion assist apparatus comprising:
a first orthosis adapted to be attached to a leg of a user;
a second orthosis adapted to be attached to an upper body of the user;
a first frame connected to the first orthosis;
a second frame connected to the second orthosis;
an actuator that is configured to selectively apply a force to the user through an intermediary of the first orthosis and the second orthosis by transmitting a driving force to the first frame or the second frame;
a posture estimation sensor that detects a posture angle of the upper body relative to a vertical plane having a longitudinal direction of the user defined as a perpendicular direction thereof;
a control unit that controls the drive of the actuator such that a force for reducing a deviation of the posture angle from a reference posture angle is applied to the user;
a trigger sensor that is configured to detect an occurrence of a trigger event, and
an operation unit configured to transmit a signal to the control unit when the operation unit is operated by a user;
wherein the control unit sets, as the reference posture angle, a posture angle detected by the posture estimation sensor at a time when the trigger sensor detects the occurrence of the trigger event after the control unit receives the signal from the operation unit and starts a calibration of the posture estimation sensor, or at a time when the signal from the operation unit is received.

2. The motion assist apparatus according to claim 1, wherein:
the trigger sensor is a force sensor that detects a magnitude of the force to be applied by the actuator in order to control a tilt of the upper body relative to the vertical plane, which has the longitudinal direction of the user defined as the perpendicular direction, and
the control unit is configured to drive the actuator such that a gap between the second orthosis and the user in a basic posture is reduced and sets, as the reference posture angle, the posture angle detected by the posture estimation sensor in a case where a force detected by the force sensor reaches a predetermined value or a value in a predetermined range.

3. The motion assist apparatus according to claim 1, wherein:
the trigger sensor is a setting switch through which the user inputs a signal at an arbitrary timing, and
the control unit sets, as the reference posture angle, the posture angle detected by the posture estimation sensor in a case where a signal from the setting switch is detected.

4. The motion assist apparatus according to claim 1, wherein the second orthosis has, on the user side, an abutting member which comes in contact with the user when the apparatus is worn by the user, and wherein a fixing position of the abutting member can be changed in a vertical direction with respect to the second frame.

5. A motion assist apparatus comprising:
a first orthosis adapted to be attached to a leg of a user;
a second orthosis adapted to be attached to an upper body of the user;
a first frame connected to the first orthosis;
a second frame connected to the second orthosis;
an actuator that is configured to selectively apply a force to the user through an intermediary of the first orthosis and the second orthosis by transmitting a driving force to the first frame or the second frame;
a posture estimation sensor that detects a posture angle of the upper body relative to a vertical plane having a longitudinal direction of the user defined as a perpendicular direction thereof;
a control unit that controls the drive of the actuator such that a force for reducing a deviation of the posture angle from a reference posture angle is applied to the user; and
a trigger sensor that is configured to detect an occurrence of a trigger event,
wherein the control unit is configured to set, as the reference posture angle, a posture angle
detected by the posture estimation sensor at a time when the trigger sensor detects the occurrence of the trigger event,
and wherein the second orthosis has, on the user side, an abutting member which comes in contact with the user when the apparatus is worn by the user, and the abutting member has a round shape as observed from a side of the user.

6. A motion assist apparatus comprising:
a first orthosis adapted to be attached to a leg of a user;
a second orthosis adapted to be attached to an upper body of the user;
a first frame connected to the first orthosis;
a second frame connected to the second orthosis;
an actuator that is configured to selectively apply a force to the user through an intermediary of the first orthosis and the second orthosis by transmitting a driving force to the first frame or the second frame;
a posture estimation sensor that detects a posture angle of the upper body relative to a vertical plane having a longitudinal direction of the user defined as a perpendicular direction thereof;
a control unit that controls the drive of the actuator such that a force for reducing a deviation of the posture angle from a reference posture angle is applied to the user; and
a trigger sensor that is configured to detect an occurrence of a trigger event,
wherein the control unit is configured to set, as the reference posture angle, a posture angle detected by the posture estimation sensor at a time when the trigger sensor detects the occurrence of the trigger event,
and wherein an abutting member is installed at a portion of the second orthosis that is abutted against the user, and the abutting member is rotatable about an axis line parallel to a lateral direction of the user with respect to the second orthosis.

7. A motion assist apparatus comprising:
a first orthosis adapted to be attached to a leg of a user;
a second orthosis adapted to be attached to an upper body of the user;
a first frame connected to the first orthosis;
a second frame connected to the second orthosis;
an actuator that is configured to selectively apply a force to the user through an intermediary of the first orthosis and the second orthosis by transmitting a driving force to the first frame or the second frame;
a posture estimation sensor that detects a posture angle of the upper body relative to a vertical plane having a longitudinal direction of the user defined as a perpendicular direction thereof;
a control unit that controls the drive of the actuator such that a force for reducing a deviation of the posture angle from a reference posture angle is applied to the user; and
a trigger sensor that is configured to detect an occurrence of a trigger event,
wherein the control unit is configured to set, as the reference posture angle, a posture angle detected by the posture estimation sensor at a time when the trigger sensor detects the occurrence of the trigger event,
wherein the second orthosis has an abutting member, which comes in contact with the user, on a front side of the user, when the apparatus is worn by the user, and wherein:
the abutting member has a size, in a lateral direction, which covers an area from a joint part of a sixth rib on a right side of the user and a sixth costal cartilage on the right side of the user, to a joint part of a sixth rib on a left side and a sixth costal cartilage on the left side,
and an area from a joint part of a seventh rib on the right side of the user and a seventh costal cartilage on the right side of the user to a joint part of a seventh rib on the left side and a seventh costal cartilage on the left side,
and the abutting member has a size, in a vertical direction, which covers an area from the joint part of the sixth rib on the right side of the user and the sixth costal cartilage on the right side of the user to a joint part of the seventh rib on the right side and the seventh costal cartilage on the right side,
and an area from the joint part of the sixth rib on the left side of the user and the sixth costal cartilage on the left side of the user to the joint part of the seventh rib on the left side and the seventh costal cartilage on the left side.

* * * * *